(12) United States Patent
Brin

(10) Patent No.: US 7,655,625 B2
(45) Date of Patent: Feb. 2, 2010

(54) METHODS OF TREATING BLEPHAROSPASM USING CYCLOSPORINE COMPONENTS

(75) Inventor: Mitchell F. Brin, Newport Beach, CA (US)

(73) Assignee: Allergan, Inc., Irvine, CA (US)

(*) Notice: Subject to any disclaimer, the term of this patent is extended or adjusted under 35 U.S.C. 154(b) by 538 days.

(21) Appl. No.: 11/673,867

(22) Filed: Feb. 12, 2007

(65) Prior Publication Data

US 2007/0191266 A1  Aug. 16, 2007

Related U.S. Application Data

(60) Provisional application No. 60/773,285, filed on Feb. 13, 2006.

(51) Int. Cl.
*A61K 38/13* (2006.01)
(52) U.S. Cl. .......................................................... 514/11
(58) Field of Classification Search ................ None
See application file for complete search history.

(56) References Cited

U.S. PATENT DOCUMENTS 5,411,952 A * 5/1995 Kaswan ........................ 514/11
7,135,455 B2 * 11/2006 Stern et al. ................... 514/11
7,151,085 B2 * 12/2006 Stern et al. ................... 514/11
7,368,426 B2 * 5/2008 Stern et al. ................... 514/11
2004/0106546 A1  6/2004 Napoli

FOREIGN PATENT DOCUMENTS

EP  1591129  12/1994
WO  WO00/61168  10/2000

OTHER PUBLICATIONS

KirschenMcLoon, et al., "Cyclosporing Protests the Eyelid Skin From Injury After Injection of Doxorubicin," Investigative Ophtalmology & Visual Sicence, Jun. 1995, vol. 36, No. 7, pp. 1433-1440 XP002439304.

* cited by examiner

*Primary Examiner*—Andrew D Kosar
(74) *Attorney, Agent, or Firm*—Joel B. German; Dean G. Stathakis; Debra D. Condino

(57) ABSTRACT

Methods of treating humans or animals afflicted with primary blepharospasm, for example, benign essential blepharospasm, or secondary blepharospasm not caused by an ocular surface disease or condition, are component to a human or animal so afflicted.

17 Claims, No Drawings

METHODS OF TREATING BLEPHAROSPASM USING CYCLOSPORINE COMPONENTS

RELATED APPLICATIONS

This application claims the benefit of U.S. Provisional Application Ser. No. 60/773,285, filed Feb. 13, 2006, the disclosure of which is hereby incorporated in its entirety herein by reference.

FIELD AND BACKGROUND OF THE INVENTION

The present invention relates to methods of providing desired therapeutic effects to humans or animals using compositions including cyclosporine components. More particularly, the invention relates to methods of treating blepharospasm, for example, primary blepharospasm and/or benign essential blepharospasm, comprising administering to a human or animal afflicted with or having such blepharospasm a therapeutically effective amount of a cyclosporine component.

The use of cyclosporine A and cyclosporin A derivatives to treat ophthalmic conditions has been the subject of various patents, for example Ding et al U.S. Pat. No. 5,474,979; Garst U.S. Pat. No. 6,254,860; and Garst U.S. Pat. No. 6,350,442, this disclosure of each of which is incorporated in its entirely herein by reference.

In addition, a number of prior art patents have disclosed the use of cyclosporine, administered topically and/or systemically, as a treatment for other conditions and/or diseases.

Blepharospasm is a term used to describe a disease characterized by involuntary, inappropriate and/or excessive, forceful eye closure. It typically affects both eyes symmetrically, although sometimes there is marked asymmetry. Blepharospasm is an adult-onset focal dystonia characterized by involuntary muscle contractions, for example, contractions of the orbicularis oculic muscles. Benign essential blepharospasm (BEB) often is used to refer to a disease characterized by primary, bilateral blepharospasm without the involvement of the lower facial musculature. When blepharospasm is associated with oromandibular dystonia, laryngeal or cervical dystonia, the complex is called segmental cranial dystonia, or Meige's syndrome.

Primary blepharospasm, for example, BEB, like other presentations of focal, adult-onset idiopathic dystonia, typically begins insidiously in the $5^{th}$ to $7^{th}$ decade of life. Estimates of the prevalence of blepharospasm range from 16 to 133 per million people, and it is more common in women. Disease progression is generally very slow and although it usually remains focal, over decades the dystonic features may spread to nearby facial muscles or, less commonly, to other parts of the body. There may be a family history of blepharospasm, other focal dystonias, movement disorder or tics. Indeed, the fundamental cause or etiology of primary blepharospasm is typically unknown and it is therefore referred to as "idiopathic", or idiopathic blepharospasm.

There may be a long prodrome of sensory symptoms such as photophobia and ocular discomfort. Initially, the dystonic muscle contractions are intermittent. If the disease progresses, the blepharospasm can increase in both frequency and intensity, leading to functional blindness in some patients. However, in the absence of therapy, some patients can have a protracted progression of symptoms. Primary blepharospasm may be task specific and occur mainly with certain activities, and not with others. It may be worse in bright light, and when the patient is tired, anxious or particularly needs to see. Many patients complain of worsening symptoms as the day wears on.

As with other focal dystonias, primary or idiopathic blepharospasm can be a prominent component of generalized primary (idiopathic torsion dystonia) and symptomatic dystonias.

For movement disorders in general, and for blepharospasm in this particular situation, we classify the disorder as a "primary" or "idiopathic" condition or a "secondary" or "symptomatic" condition. Idiopathic means without a known etiology or the presence of any other disorder that can present with the symptoms. Patients with idiopathic disease have no evidence by history, examination, or laboratory studies of any identifiable cause for the dystonic symptoms. Therefore, such patients have a normal perinatal and early developmental history, no prior history of neurologic illness or exposure to drugs known to cause acquired dystonia (e.g., phenothiazines), normal intellectual, pyramidal, cerebellar, and sensory examinations, and normal diagnostic studies. Patients who have abnormalities, such as those noted above, are classified as having secondary or symptomatic dystonia. In the case of blepharospasm, some patients present with evidence of one or more ocular surface conditions. However, the diagnosis of primary blepharospasm can be made with confidence when the increased eyeblinking persists after the ocular surface condition or conditions are treated.

Blepharospasm is seen in about a quarter of patients with progressive supranuclear palsy. This is an example of symptomatic blepharospasm. In patients with Parkinson's disease, an exaggerated blink reflex is through to be the basis of the Meyerson's sign, also known at the glabellar tap sign. Infrequently, patients with Parkinson's disease have significant blepharospasm superimposed on their hypomimia. Dystonic facial grimacing is also seen as a dystonic hyperkinesia associated with levodopa therapy. Secondary blepharospasm sometimes occurs in tardive dystonia.

The diagnosis of primary blepharospasm, such as BEB, is made on a typical history, even prior to the examination for physical signs. Patients may present to ophthalmologists with sore eyes. Even if slit lamp examination of the eyelids reveals chronic ocular surface disorders such as blepharitis, meibomian gland dysfunction or dry eyes, appropriate local treatment usually has no effect on the primary symptoms. It is possible that these disorders trigger primary blepharospasm in individuals who are genetically or otherwise susceptible.

Secondary blepharospasm may result from local ocular surface or oculosurface disease, for example, corneal irritation, corneal abrasions, keratoconjunctivitis sicca (dry eye) and the like. However, the characteristic fluctuations experienced by patients in primary or idiopathic blepharospasm are not evident in patients with this type of local oculosurface disease associated blepharospasm.

Thus, primary blepharospasm, for example, BEB, is different and distinct from blepharospasm associated with local oculosurface disease.

A study has been reported, in Sansom, J. et al, Treatment of Keratoconjunctivitis Sicca in Dogs with Cyclosporine Ophthalmic Ointment: a European Clinical Field Trial, The Veterinary Record, Nov. 11, 1995, in which dogs suffering from secondary blepharospasm caused by keratoconjunctivitis sicca were treated with cyclosporine ophthalmic ointment. The incidence of secondary blepharospasm, as well as other signs of discomfort and corneal oedema, was reported in this study as having decreased significantly over the course of the study.

A number of treatments have been suggested for primary blepharospasm. For example, injections of botulinum toxin have been found to be effective. Also, various drugs have been reported to be effective. Such drugs include:

Benzodiazepines (diazepam, clonazepam, lorazepam, oxazepam)

Anticholinergics (orphenadrine, trihexyphenidyl)

Serotonin antagonists (cyproheptadine)
Antipsychotics (phenothiazine, butyrophenone, reserpine)
Affective disorder agents (lithium carbonate, tetrabenazine)
Antianxiety agents (meprobamate)
Stimulants (amphetamine)
Sedatives (phenobarbital)
Parasympathomimetics (lecithin, choline, physostigmine)
Antimuscarinics (tincture of belladonna, scopolamine)
Antihistamines (diphenhydramine hydrochloride)
Gamma aminobutyric acid (GABA) agonists (baclofen)

There continues to be a need for new methods of treating blepharospasm, for example, blepharospasm not caused by oculosurface disease, for example, not caused by keratoconjunctivitis sicca, such as primary blepharospasm, secondary blepharospasm in Parkinson's disease and secondary blepharospasm in tardive dystonia.

SUMMARY OF THE INVENTION

New methods of treating blepharospasm in humans or animals have been discovered. The present methods provide substantial overall efficacy in providing the desired therapeutic effect or effects. In addition, other important benefits are obtained employing the present methods. For example, the present methods can be easily and effectively practiced by the prescribing physician and patient without causing substantial or undue patient stress. In short, the present methods provide substantial and acceptable overall efficacy, together with other advantages, such as ease of practice and reduced patient stress.

In one aspect of the present invention, the present methods comprise administering a therapeutically effective amount of a cyclosporine component to a human or animal afflicted with, for example, suffering from or having, blepharospasm not resulting from local ocular surface or oculosurface disease. The administering step is effective in treating the blepharospasm. In one useful embodiment, the human or animal is afflicted with blepharospasm selected from primary blepharospasm, secondary blepharospasm in Parkinson's disease or secondary blepharospasm in tartive dystonia.

In another aspect of the invention, the present methods comprise administering a therapeutically effective amount of a cyclosporine component to a human or animal afflicted with blepharospasm which is not caused by keratoconjunctivitis sicca, i.e., dry eye syndrome. The administering step is effective in treating the blepharospasm.

The administering step may comprise locally or topically administering the cyclosporine component to the blepharospasm afflicted human or animal, for example and without limitation, locally or topically administering the cyclosporine component to at least one of an eye and an eyelid of the afflicted human or animal. The cyclosporine component may be administered, for example, locally or topically administered, to one eye and/or eyelid or both eyes and/or eyelids of the afflicted human or animal.

Each and every feature described herein, and each and every combination of two or more of such features, is included within the scope of the present invention provided that the features included in such a combination are not mutually inconsistent.

These and other aspects and advantages of the present invention are apparent in the following detailed description, examples and claims.

DETAILED DESCRIPTION

The present methods employ cyclosporine components to treat humans or animals, for example, other mammals, afflicted with blepharospasm, for example, blepharospasm not resulting from local ocular surface or oculosurface disease, blepharospasm other than that caused by dry eye syndrome, and the like. Examples of blepharospasm which can be treated in accordance with the present invention include primary blepharospasm, for example, BEB and other forms of primary blepharospasm, and secondary blepharospasm, such as secondary blepharospasm in Parkinson's disease, secondary blepharospasm in tardive dystonia and the like. In general, the present methods comprise administering a therapeutically effective amount of a cyclosporine component to a human or animal afflicted, e.g., suffering from or having, blepharospasm to be treated. The administering step is effective to treat the blepharospasm.

Blepharospasm is treated in accordance with the present invention when, for example and without limitation, as a result of the present administering step, one or more symptoms of the blepharospasm is reduced in severity or eliminated, the progression of the blepharospasm is slowed or stopped or reversed, the blepharospasm itself is reduced in severity or substantially (or totally) resolved and the like therapeutic benefits.

In one embodiment, the present administering step comprises locally, for example, without limitation, topically, administering the cyclosporine component to the affected area, for example, the eye or eyes and/or eyelid or eyelids, of the human or animal. Local, e.g., topical, administration allows a therapeutically effective amount of the cyclosporine component to be administered to treat a condition, without subjecting the remainder of the human or animal to the cyclosporine component.

Employing reduced systemic or blood concentrations of cyclosporine component, as in one embodiment of the present invention, is advantageously effective to treat the blepharospasm under treatment, preferably with substantially no detectable concentration of the cyclosporine component in the blood of the human or animal being treated. The cyclosporine component concentration of blood can be advantageously measured using a validated liquid chromatography/mass spectrometry-mass spectrometry (VLC/MS-MS) analytical method, such as described elsewhere herein.

In one embodiment, in the present methods the blood of the human or animal has concentrations of clycosporin component of 0.1 ng/ml or less.

In one embodiment, the cyclosporine component may be administered to a human or animal as part of the combination treatment to treat blepharospasm of the human or animal. For example, the cyclosporine component may be administered to the human or animal along with one or more other therapeutic agents effective in treating blepharospasm of the human or animal. The other therapeutic agent or agents can be administered to the human or animal in the same composition with the cyclosporine component or in a different composition from the cyclosporine component. Examples of useful other therapeutic components include, without limitation, antibiotics, various pain medications, anti-inflammatory medications and the like and mixtures thereof.

Any suitable cyclosporine component effective in the present methods may be used.

Cyclosporines are a group of nonpolar cyclic oligopeptides with known immunosuppressant activity. Cyclosporin A, along with several other minor metabolites, as well as cyclosporin B, C, D, E, F, G, H, I, J, K, L, M, N, O, P, Q, R, S, T, U, V, W, X, Y and Z, have been identified. In addition, derivatives, salts and the like of such cyclosporines and a number of synthetic analogs have been prepared and may be useful in the present invention. See, for example, the Garst Patents noted elsewhere herein.

In general, commercially available cyclosporines may contain a mixture of several individual cyclosporines which all share a cyclic peptide structure consisting of eleven amino acid residues with a total molecular weight of about 1,200, but with different substituents or configurations of some of the amino acids.

The term "cyclosporine component" as used herein is intended to include any individual member of the cyclosporine group, salts thereof, derivatives thereof, analogs thereof and mixtures thereof, as well as mixtures of two or more individual cyclosporines salts thereof, derivatives thereof, analogs thereof and mixtures thereof.

Particularly preferred cyclosporine components include, without limitation, cyclosporin A, derivatives of cyclosporin A, salts of cyclosporin A and the like and mixtures thereof. Cyclosporin A is an especially useful cyclosporine component.

The chemical structure for cyclosporin A is represented by Formula 1

As used herein the term "derivatives" of a cyclosporine refer to compounds having structures sufficiently similar to the cyclosporine so as to function in a manner substantially similar to or substantially identical to the cyclosporine, for example, cyclosporine A, in the present methods. Included, without limitation, within the useful cyclosporine A derivatives are those selected from ((R)-methylthio-Sar)$^3$-(4'-hydroxy-MeLeu) cyclosporine A, ((R)-(Cyclo)alkylthio-Sar)$^3$-(4'-hydroxy-MeLeu)$^4$-cyclosporine A, and ((R)-(Cyclo)alkylthio-Sar)$^3$-cyclosporine A derivatives described below.

These cyclosporine derivatives are represented by the following general formulas (II), (III), and (IV) respectively:

Formula I

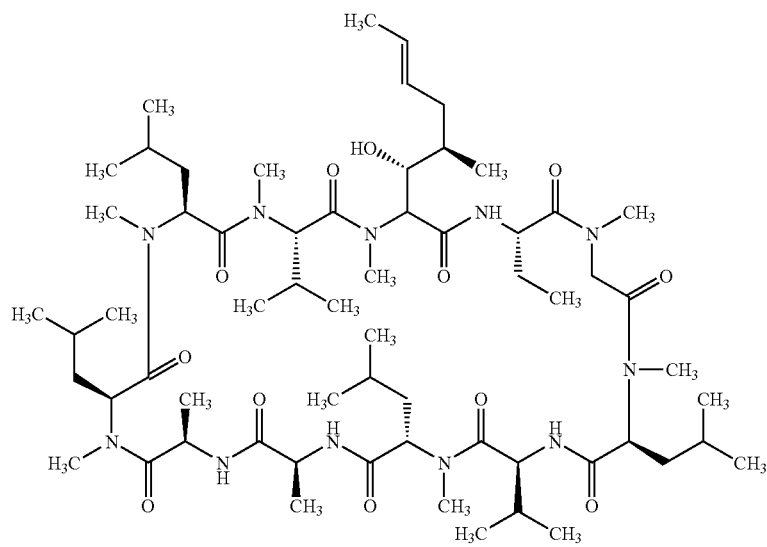

Formula II

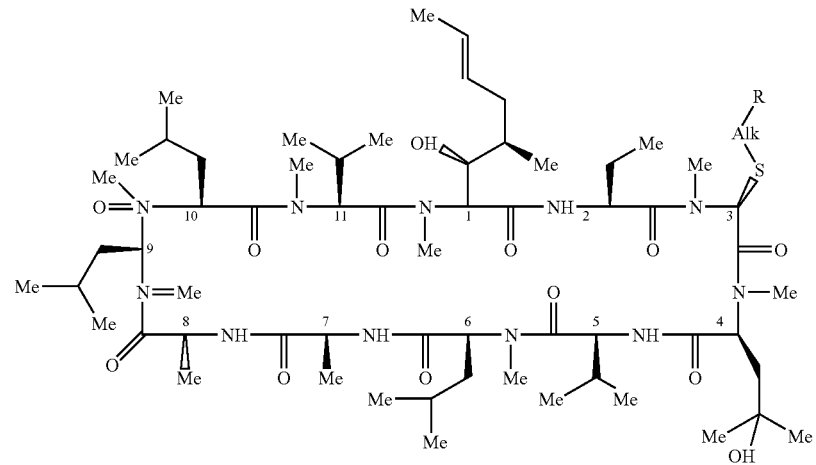

(II)

-continued

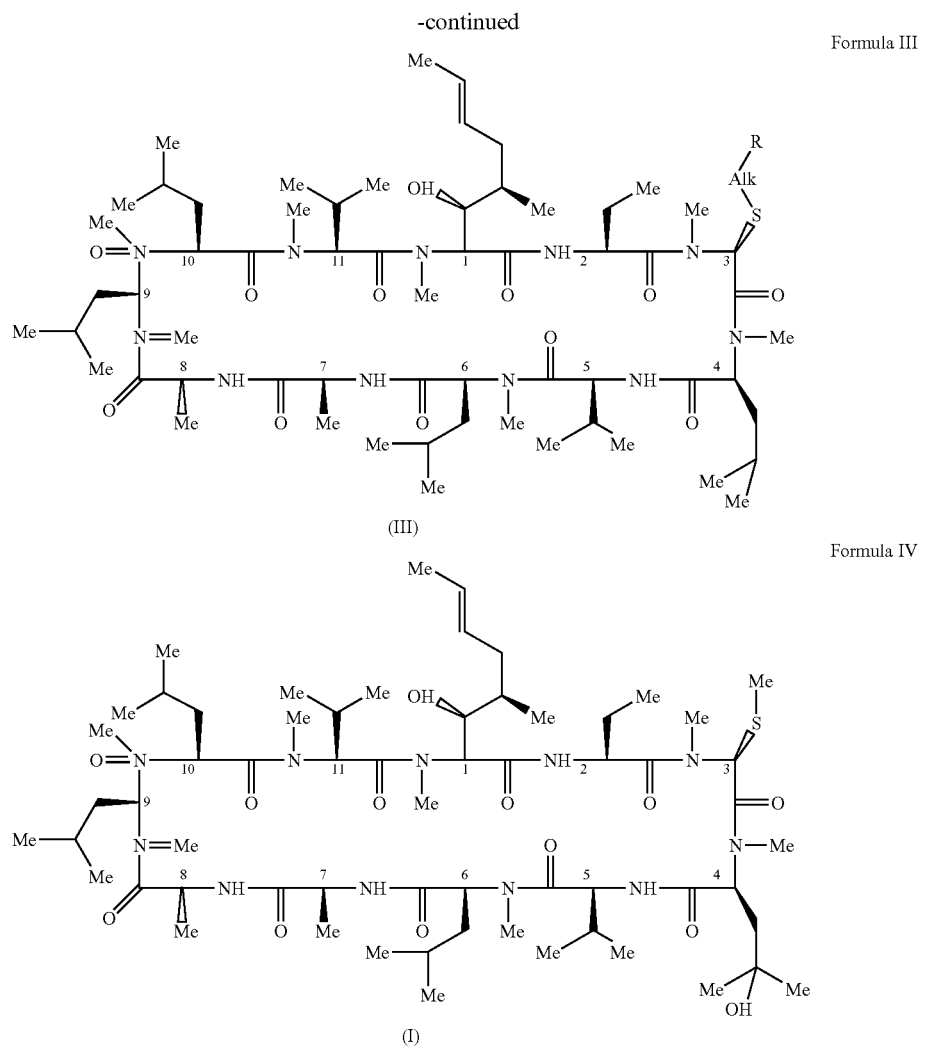

Formula III (III)

Formula IV (I)

wherein Me is methyl; Alk is 2-6C alkylene or 3-6C cycloalkylene; R is OH, COOH, alkoxycarbonyl, —NR$_1$R$_2$ or N(R$_3$)—(CH$_2$)—NR$_1$R$_2$; wherein R$_1$,R$_2$ is H, alkyl, 3-6C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1-3 heteroatoms; or NR$_1$R$_2$ is a 5 or 6 membered heterocycle which may contain a further N, O or S heteroatom and may be alkylated; R$_3$ is H or alkyl and n is 2-4; and the alkyl moieties contain 1-4C.

The present methods may be practiced employing any suitable compositions or combinations of compositions including therapeutically effective amounts of cyclosporine component. The cyclosporine component is present in an amount effective to provide the desired therapeutic effect when the cyclosporine-containing composition is administered to a human or animal in accordance with the present invention. The cyclosporine component advantageously is present in the compositions in amounts ranging from about 0.03% to about 15% or about 20% or more by weight of the composition. In one embodiment, the cyclosporine component is present in an amount of about 0.1% to about 5% or about 10% or about 15% by weight of the composition. It is intended, however, that the choice of a particular amount of cyclosporine component is to be made in accordance with factors well known in the medicinal arts, including mode of administration, the size and condition of the human or animal and the type and severity of the condition to be treated.

The presently useful compositions may be liquids, suspensions, emulsions, semi-solids, gels, lotions, ointments, creams and the like. Those skilled in the art of pharmaceutical formulation are able to formulate suitable compositions including cyclosporine components in a suitable form, such as those forms noted herein, for example, including one or more pharmaceutically acceptable excipients, such as those conventionally used in similar compositions. Of course, care should be taken to use composition components which are compatible with the cyclosporin component being used and which do not unduly or significantly interfere with the administering step in which the composition is being used or with the human or animal being treated.

For example, cyclosporine components can be combined with carriers which form emulsions upon mixing with water. Such emulsions are described, for example, and without limitation, in Cavanak U.S. Pat. No. 4,388,307, the disclosure of which is hereby incorporated in its entirety herein by reference. Carriers, for example, and without limitation, glyceride carriers, may assist in alleviating problems of physical instability such as precipitation of the cyclosporine component from solution, and may also enable higher blood plasma concentrations, if desired.

In a useful embodiment, the presently useful compositions include hydrophobic components. Any suitable hydrophobic component may be employed in the present invention. Advantageously, the cyclosporine component is solubilized in the hydrophobic component. In one embodiment, the hydrophobic component may be considered as comprising a discontinuous phase in the presently useful cyclosporine component-containing compositions, for example, oil-in-water emulsions.

The hydrophobic component may be present in an effective amount, for example, in an amount of up to about 1.0% by weight or about 1.5% by weight or more of the composition.

Preferably, the hydrophobic component comprises one or more oily materials. Examples of useful oil materials include, without limitation, vegetable oils, animal oils, mineral oils, synthetic oils and the like and mixtures thereof. In a very useful embodiment, the hydrophobic component comprises one or more higher fatty acid glycerides. Excellent results are obtained when the hydrophobic component comprises castor oil.

Other useful cyclosporine component-containing compositions comprise the cyclosporine component in admixture with an emulsifying amount of a fatty acid glyceride, such as castor oil and the like, and a surfactant, such as polysorbate 80. Such compositions are described in Ding et al U.S. Pat. No. 5,474,979, the disclosure which is hereby incorporated in its entirety herein by reference. Also see Kaswan U.S. Pat. No. 4,649,047 and Kaswan U.S. Pat. No. 5,411,952, the disclosure of each of which is hereby incorporated in its entirety herein by reference.

In one embodiment, the presently useful compositions are self-emulsifying which, when exposed to an aqueous medium, form fine oil-in-water emulsions with little or no agitation. Additionally, emulsions may be prepared by combining a self-emulsifying pre-concentrate with an aqueous medium.

Previously-disclosed self-emulsifying systems include those in which a cyclosporine component is combined with mixtures of (i) medium-chain triglycerides and nonionic surfactants, (ii) vegetable oils and partial glycerides, such as polyglycolized glycerides or medium-chain mono- and diglycerides, or (iii) vegetable oils and nonionic surfactants such as polysorbate 80 or PEG-25 glyceryl trioleate.

In certain self-emulsifying formulations, a "microemulsion preconcentrate" of a cyclosporine component is formed by combining the cyclosporine component with (I) a hydrophilic phase, (II) a lipophilic phase, and (III) a surfactant, as well as optional thickeners, antioxidants or other excipients. Examples of such compositions are disclosed in Hauer et al U.S. Pat. No. 5,342,625, the disclosure which is hereby incorporated in its entirety herein by reference.

In addition, suitable compositions may include cyclosporine components in combination with a hydrophilic solvent phase and one or more surfactants, but not containing lipophilic solvents. Such cyclosporine component-containing formulations may be stable, simple to prepare, and have good pharmacokinetic properties.

As used herein, the terms "binary system", "binary composition" and "binary system of excipients" denote those cyclosporine component-containing formulations and compositions which contain, in addition to the cyclosporine component, a combination of at least one hydrophilic solvent and at least one surfactant, but which lack a lipophilic solvent. Such compositions may be supplemented with additional adjuvants and still be considered "binary", so long as they do not include a lipophilic solvent phase.

To prepare such pharmaceutical compositions, a binary system is combined with a cyclosporine component. The hydrophilic phase may comprise one or more of the known pharmaceutically acceptable hydrophilic solvents or excipients that are capable of solubilizing the cyclosporine component. Suitable classes of hydrophilic compounds include, for example and without limitation, pharmaceutically acceptable alcohols including the polyethylene glycols.

Examples of hydrophilic phase components useful in the presently useful compositions include, but are not limited to, water, ethanol, benzyl alcohol, propylene glycol, low molecular weight polyethylene glycols having a molecular weight of up to about 1,000, glycol, dimethyl isosorbide and the like and mixtures thereof.

The hydrophilic phase, comprising one or more hydrophilic solvents, typically comprises about 10% to about 90% by weight of the pharmaceutical composition. The precise amount used will vary depending on the nature of the hydrophilic compound or compounds used, the amount of cyclosporine component present, the dosage form, the condition being treated and other factors known in the art. Preferably the hydrophilic phase comprises about 20% to about 80%, and more preferably about 30% to about 60%, by weight of the composition. Where non-aqueous hydrophilic components are used, water can be included in the formulation at levels varying from about 0.5% to about 10%, or preferably from about 1% to about 5%, based on total weight of the composition.

Any of the known pharmaceutically acceptable surfactants may be used, including nonionic, anionic, cationic, and combinations thereof. Nonionic surfactants are preferred, and especially those surfactants having a hydrophile/lipophile balance (HLB) of 10 or more. Alternatively, certain combinations of high- and low-HLB surfactants may be utilized; preferably, such mixed surfactants are used in ratio such that the aggregate surfactant HLB (when weighted according to proportions used) remains in excess of 10.

Examples of suitable surfactants include, but are not limited to, polyoxyethylene derivatives of natural or hydrogenated vegetable oils such as castor oil; polyoxyethylene-sorbitan fatty acid esters, such as mono-, di- and tri-lauryl, palmityl, stearyl and oleyl esters; alkyl/dialykyl sulfate, sulfonate or sulfosuccinate salts such as sodium lauryl sulfate and dioctyl sodium sulfosuccinate; polyoxyethylene fatty acid esters; phospholipids such as lecithins; transesterification products of natural vegetable oil triglycerides and polyalkylene polyols; sorbitan fatty acid esters; pentaerythritol fatty acid esters; polyoxyethylene glycol alkyl ethers and esters; and the like. The surfactants may be used alone or in combination.

Examples of specific surfactants which may be used include, without limitation, polyoxyethylene castor oil derivatives, such as polyoxyethylene glycerol triricinoleate polyoxyl 35 castor oil (CREMOPHOR® EL, available from BASF Corporation), and polyoxyl 40 hydrogenated castor oil (CREMOPHOR® RH40, available from BASF Corporation); mono-fatty acid esters of poloxyethylene (20) sorbitan, such as polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), and polyoxyethylene(20) sorbitan monolaurate (TWEEN® 20) (all available from ICI Surfactants, Wilmington, Del.); polyoxyethylene glycol 200 monostearate (MYRJ® 52, available from Calgene Chemicals, Skokie, Ill.); polyglycerol esters with a HLB of 10 or greater, such as decablyceryl mono- and dioleate and the like; and mixtures thereof.

In some instances (as when the compositions are prepared as semi-solids), it may be advantageous to use at least one additional low-HLB surfactant along with one or more of the above high-HLB surfactant. Examples of low-HLB auxiliary surfactants which may be used include, but are not limited to, polyglycerol oleates (such as CAPROL® 10G40); lecithins; glyceryl monooleate or monolinoleate mixtures (such as MYVEROL® 18-99 or 18-92); propylene glycol laurate; and sorbitan oleates such as sorbitan monooleate (SPAN® 80), sorbitan trioleate (SPAN® 85), and sorbitan sesquioleate (SPAN® 20) (all available from ICI Surfactants, Wilmington, Del.).

The surfactant phase may comprise about 10% to 90% by weight of the composition. Preferably the surfactant comprises about 20% to about 70% of the composition, and more preferably about 40% to about 60%, by weight.

If desired, the presently useful compositions may additionally comprise other pharmaceutically acceptable excipients, such as tonicity components, buffer components, polyelectrolyte components, thickeners, fillers, diluents, flavoring agents, coloring agents, antioxidants, preservatives, such as antibacterial or antifungal agents, acids and/or basis to adjust pH, and the like and mixtures thereof. Such additives, if present, may typically comprise about 0.01% to about 10% by weight of the composition. Such additives include those additives which are conventional and/or well known for use in similar pharmaceutical compositions. For example, suitable thickening agents include any of those known in the art, as for example pharmaceutically acceptable polymers and/or inorganic thickeners. Such agents include, but are not limited to, polyacrylate homo- and co-polymers; celluloses and cellulose derivatives; polyvinyl pyrrolidones; polyvinyl resins; silicates; and the like and mixtures thereof.

When desired, the cyclosporine-containing compositions may be prepared as semi-solid rather than liquid formulations by addition a greater proportion of appropriate thickening or solidifying agents. Solidifiers suitable for the preparation of semi-solid compositions include, but are not limited to, polyethylene glycols having a molecular weight of more than about 1,000, such as PEG 1450 and PEG 3350; stearyl alcohol; and colloidal silicon dioxide (CAB-O-SILO® M-5, available from Cabot, Tuscola, Ill.). A semi-solid state may be often obtained by adding between about 8% or about 10% and about 15% or about 25% by weight solidifying agent. The actual amount of solidifying agent needed will depend on the physical characteristics of the other excipients which are present.

Useful cyclosporine component-containing compositions include those disclosed in U.S. Patent Publication No. 2005/0059583, the disclosure of which is hereby incorporated in its entirety herein by reference.

Except as otherwise noted elsewhere herein, the cyclosporine component-containing compositions may be administered, for example and without limitation, locally or topically, for example and without limitation, by any of the methods known in the art. Such methods include, but are not limited to, parenteral administration including intravenous injection or infusion of a cyclosporine component-containing composition; and/or topical administration methods, such as topical administration of ointments, drops, solutions, suspensions or emulsions including a cyclosporine component. Topical formulations, for example, intended for administration to the eyes or eyelids, may be prepared directly, or by combining a cyclosporine component-containing concentrate with a diluent, for example, an aqueous diluent. Such topical formulations may include additional excipients as necessary, for example, to modify consistency of the rate of absorption of the cyclosporine component.

The following non-limiting examples illustrate certain aspects of the present invention.

EXAMPLE 1

A female patient, age 60, suffering from primary blepharospasm, and presenting no evidence of keratoconjunctivitis sicca (dry eye syndrome), is treated by administering in both eyes 2 or 3 drops of an eye drop composition in the form of an emulsion containing 0.2% by weight of cyclosporine A in a castor oil/water-containing carrier. This treatment is repeated two times daily for 5 weeks. After this period of treatment, the patient reports a reduction in at least one symptom of the primary blepharospasm.

EXAMPLE 2

A female patient, age 55, is diagnosed with benign essential blepharospasm. The patient shows no evidence of keratoconjunctivitis sicca (dry eye syndrome). The patient is treated by administering in both eyes 2 or 3 drops of an eye drop composition in the form of an emulsion comprising 0.2% by weight of cyclosporin A in a castor oil/water-containing carrier. This treatment is repeated twice daily for a month. After this time of treatment, the patient reports a reduction in at least one symptom of the benign essential blepharospasm.

EXAMPLE 3

A male patient, age 45, is found to have blepharospasm. Upon examination of the patient, he is determined not to be suffering or having dry eye syndrome. The patient is treated by administering in both eyes 2 or 3 drops of an eye drop composition in the form of an emulsion containing 0.2% by weight of cyclosporin A in a castor oil/water-containing carrier. This treatment is repeated twice daily for two months. After this period of treatment, the patient reports a reduction in at least one symptom of the blepharospasm.

EXAMPLE 4

A male patient, age 67, is diagnosed with Parkinson's disease. He develops symptoms of blepharospasm which are related to or caused by the Parkinson's disease. Upon examination of the patient, he is determined not to be suffering or having dry eye syndrome or any other ocular surface condition. The patient is treated by administering in both eyes 2 or 3 drops of an eye drop composition in the form of an emulsion containing 0.2% by weight of cyclosporin A in a castor oil/water-containing carrier. This treatment is repeated twice daily for two months. After this period of treatment, the patient reports a reduction in at least one symptom of the blepharospasm.

EXAMPLE 5

A female patient, age 63, is diagnosed with tardive dystonia. Upon examination, it is determined that the patient suffers from blepharospasm which is caused by the tardive dystonia. Upon examination of the patient, she is determined not to be suffering or having dry eye syndrome or any other ocular surface condition. The patient is treated by administering in both eyes 2 or 3 drops of an eye drop composition in the form of an emulsion containing 0.2% by weight of cyclosporin A in a castor oil/water-containing carrier. This treatment is repeated twice daily for two months. After this period of treatment, the patient reports a reduction in at least one symptom of the blepharospasm.

EXAMPLES 6 TO 10

Examples 1 to 5 are repeated except that the composition administered to both eyes of the patient is about 30 mg of an ophthalmic ointment containing 0.2% by weight of cyclosporine A in a conventional ophthalmically acceptable ointment base. The therapeutic benefits obtained by the patients in Examples 6 to 10 are similar to those obtained by the patients in Examples 1 to 5, respectively.

While this invention has been described with respect to various specific examples and embodiments, it is to be understood that the invention is not limited thereto and that it can be variously practiced within the scope of the following claims.

What is claimed is:

1. A method of treating blepharospasm, the method comprising:
administering a therapeutically effective amount of a cyclosporine component selected from the group consisting of cyclosporin A, salts thereof and mixtures thereof to a human or animal afflicted with blepharospasm not resulting from local oculosurface disease, the administering step being effective in treating the blepharospasm.

2. The method of claim 1 wherein the human or animal is afflicted with blepharospasm selected from the group consisting of primary blepharospasm, secondary blepharospasm in Parkinson's disease, and secondary blepharospasm in tardive dystonia.

3. The method of claim 1 wherein the human or animal is afflicted with secondary blepharospasm in Parkinson's disease.

4. The method of claim 1 wherein the human or animal is afflicted with blepharospasm in tardive dystonia.

5. The method of claim 1 wherein the human or patient is afflicted with primary blepharospasm.

6. The method of claim 5 wherein the human or animal is afflicted with benign essential blepharospasm.

7. The method of claim 1 wherein the administering step comprises locally administering the cyclosporine component to the human or animal.

8. The method of claim 1 wherein the administering step comprises topically administering the cyclosporine component to the human or animal.

9. The method of claim 1 wherein the administering step comprises locally administering the cyclosporine component to at least one of an eye and an eyelid of the human or animal.

10. The method of claim 1 wherein the administering step comprises topically administering the cyclosporine component to at least one of an eye and an eyelid of the human or animal.

11. The method of claim 1 wherein the cyclosporine component is cyclosporin A.

12. A method of treating blepharospasm, the method comprising:
administering a therapeutically effective amount of a cyclosporine componet selected from the group consisting of cyclosporin A, salts thereof and mixtures thereof to a human or animal afflicted with blepharospasm not caused by keratoconjunctivitis sicca, the administering step being effective in treating the blepharospasm.

13. The method of claim 12 wherein the administering step comprises locally administering the cyclosporine component to the human or animal.

14. The method of claim 12 wherein the administering step comprises topically administering the cyclosporine component to the human or animal.

15. The method of claim 12 wherein the administering step comprises locally administering the cyclosporine component to at least one of an eye and an eyelid of the human or animal.

16. The method of claim 12 wherein the administering step comprises topically administering the cyclosporine component to at least one of an eye and an eyelid of the human or animal.

17. The method of claim 12 wherein the component is cyclosporine A.

* * * * *

UNITED STATES PATENT AND TRADEMARK OFFICE
CERTIFICATE OF CORRECTION

| | | |
|---|---|---|
| PATENT NO. | : 7,655,625 B2 | Page 1 of 1 |
| APPLICATION NO. | : 11/673867 | |
| DATED | : February 2, 2010 | |
| INVENTOR(S) | : Mitchell F. Brin | |

It is certified that error appears in the above-identified patent and that said Letters Patent is hereby corrected as shown below:

On the Title page, Item (56) under "Other Publications", in column 2, line 1, delete "Cyclosporing" and insert -- Cyclosporine --, therefor.

On the Title page, Item (56) under "Other Publications", in column 2, line 3, delete "Ophtalmology" and insert -- Ophthalmology --, therefor.

On the Title page, Item (56) under "Other Publications", in column 2, line 3, delete "Sicence," and insert -- Science, --, therefor.

On the Title page, Item (57), Abstract, in column 2, line 4, after "are"
insert -- disclosed which include administering a cyclosporine --.

In column 1, line 38, delete "oculic" and insert -- oculi --, therefor.

In column 10, line 45, delete "alkyl/dialykyl" and insert -- alkyl/dialkyl --, therefor.

In column 10, line 60, delete "poloxyethylene" and insert -- polyoxyethylene --, therefor.

In column 11, line 2, delete "decablyceryl" and insert -- decaglyceryl --, therefor.

In column 14, line 21, in Claim 12, delete "componet" and insert -- component --, therefor.

In column 14, line 39, in Claim 17, after "the" insert -- cyclosporine --.

Signed and Sealed this

Eighth Day of June, 2010

David J. Kappos
*Director of the United States Patent and Trademark Office*